United States Patent [19]

Hentschel et al.

[11] Patent Number: 5,075,444

[45] Date of Patent: Dec. 24, 1991

[54] DISODIUM SALT OF TRIMERCAPTO-S-TRIAZINE HEXAHYDRATE, AND METHOD OF ITS PREPARATION

[75] Inventors: Klaus Hentschel, Rodenbach, Fed. Rep. of Germany; Marc Samson, Lokeren, Belgium; Marcel Vingerhoets, Brecht, Belgium; Karl-Ludwig Weber, Kapellen, Belgium

[73] Assignee: Degussa AG, Fed. Rep. of Germany

[21] Appl. No.: 569,139

[22] Filed: Aug. 17, 1990

[30] Foreign Application Priority Data

Aug. 19, 1989 [DE] Fed. Rep. of Germany ....... 3927469

[51] Int. Cl.$^5$ ............................................ C07D 251/38
[52] U.S. Cl. ........................................................ 544/219
[58] Field of Search ........................................... 544/219

[56] References Cited

U.S. PATENT DOCUMENTS 3,778,368  12/1973  Nakamura et al. ................... 210/54
4,849,517   7/1989  Weber et al. ......................... 544/219
5,006,654   4/1991  Ludwig et al. ....................... 544/219

*Primary Examiner*—John M. Ford
*Attorney, Agent, or Firm*—Cushman, Darby & Cushman

[57] ABSTRACT

The disodium salt of trimercapto-s-triazine hexahydrate (TMT-Na$_2$.6H$_2$O) which has a considerably higher water solubility than previously known TMT sodium salts. It is used for separating heavy metals from aqueous phase, especially from waste water.

TMT-Na$_2$.6H$_2$O is prepared by reacting TMT-Na$_3$.9H$_2$O, available from cyanuric chloride, with trimercapto-s-triazine (TMT-Ha$_3$) in a molar ratio of 2–2.1 to 1 in aqueous medium with subsequent crystallization of the TMT-Na$_2$.6H$_2$O.

2 Claims, No Drawings

DISODIUM SALT OF TRIMERCAPTO-S-TRIAZINE HEXAHYDRATE, AND METHOD OF ITS PREPARATION

The present invention relates to the disodium salt of trimercapto-s-triazine hexahydrate, a method of its preparation and its use. The compound has the following structural formula:

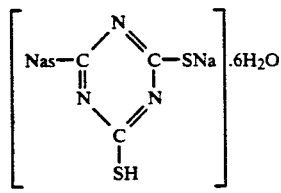

and is designated herein as "TMT-Na$_2$.6 H$_2$O".

BACKGROUND OF THE INVENTION

Trimercapt (referred to as "TMT-H$_3$" in the following description) as well as sodium salts of this trivalent acid, have been described by A.W. Hofmann - Chem. Ber. 18 (1885), 2196-2207. TMT-H$_3$ was obtained by reacting 2,4,6-trichloro-s-triazine (cyanuric chloride) with sodium sulfide followed by acidification. A monosodium salt of trimercapto-s-triazine was also isolated.

Nakamura et al. - Japan Kokai 49/1580 (Chem. Abstr. 81, 3272 b) prepared the monosodium salt of trimercapto-s-triazine in the form of the trihydrate (TMT-Na·3 H$_2$O) by reacting NaHS and Na$_2$S with cyanuric chloride in an aqueous phase.

According to Published German Patent Specification DE-AS 22 40 549, heavy metals such as e.g. Cu, Cd, Ni, Hg, Ag, Pb can be separated as slightly soluble compounds from waste water using trimercapto-s-triazine or its water-soluble alkali-metal salts. Solid TMT-Na·3 H$_2$O or a 3% by weight aqueous solution of the monosodium salt of trimercapto-s-triazine (TMT-Na) is used with preference in the exemplary comments of this document. The di- and trisodium salts of trimercapto-s-triazine (referred to as "TMT-Na$_2$" and "TMT-Na$_3$" in the following description) are also suggested as possible precipitation reagents. The saturation concentration of aqueous solutions of alkali-metal-, ammonium- and alkaline-earth metal salts of mono-, di- and trimercapto-s-triazines is given as 0.01 to 25% by weight at 25° C.

Published German Patent Application DE-AS 22 40 733 teaches a method of recovering heavy metal ions from ores, in which, among other things, an aqueous solution of trimercapto-s-triazine trisodium salt (TMT-Na$_3$) is also used. No information is given about the preparation of TMT-Na$_2$ and TMT-Na$_3$ or their solubility in water.

Aqueous solutions of TMT-Na$_3$ are commercially available and are used in particular for separating heavy metal from the flue gas wash water of power plants and garbage incinerators, from waste water in the mining industry and from galvanotechnical and chemical plants. The commercially available, aqueous TMT-Na$_3$ solution has a concentration of 15% by weight (Publication TMT 15 of the Degussa company, 3/1986). The saturation concentration of TMT-Na$_3$ in water is approximately 16% by weight at 0° C.

As is apparent from Published German Patent Application DE-OS 37 29 029, TMT-Na$_3$ was obtained for the first time as nonahydrate in crystalline form. The preparation of TMT-Na$_3$.9 H$_2$O comprises the stages of reaction of cyanuric chloride with NaHS or Na$_2$S or with an NaHS/Na$_2$S mixture in aqueous medium at a pH above 7 at 20°-70° C., subsequent adjustment of the pH to preferably around 12.5 and cooling of the reaction mixture, at which time TMT-Na$_3$.9 H$_2$O crystallizes out. After the drying, the product contains 60% by weight TMT-Na$_3$ and 40% by weight water of crystallization.

As has already been noted above, no previous document is known which describes a disodium salt of trimercapto-s-triazine in solid form.

SUMMARY OF THE INVENTION

The present invention provides a novel sodium salt of trimercapto-s-triazine, i.e., the disodium salt of trimercapto-s-triazine-hexahydrate.

Whereas TMT-H$_3$ is practically insoluble (under 0.5% by weight) and TMT-Na.3 H$_2$O is slightly soluble in water (approximately 3% by weight, calculated as TMT-Na), TMT-Na$_3$.9 H$_2$O has good solubility, which was to be expected (at 0° C. approximately 16% by weight, calculated as TMT-Na$_3$). It could not have been expected that the solubility of TMT-Na$_2$.6 H$_2$O is considerably above that of the readily soluble TMT-Na$_3$.9 H$_2$O. Whereas an aqueous solution saturated with TMT-Na$_3$.9 H$_2$O at 0° C. contains 0.78 mole TMT-Na$_3$ per liter water, the content of an aqueous solution saturated with TMT-Na$_2$.6 H$_2$O at 0° C. is approximately 2 moles TMT-Na$_2$ per liter water.

Solutions of TMT-Na$_2$.6 H$_2$O not only have a higher content of active substance (with a content of 67% by weight TMT-Na$_2$) than TMT-Na$_3$.9 H$_2$O does, but the salt of the invention also permits the preparation of more concentrated aqueous solutions which are stable during storage at lower temperatures, that is, they do not crystallize. The actual active substance of the sodium salts of TMT-H$_3$ is the trimercapto-s-triazine, so that a rather high content in the solid (mole TMT salt)/kg) and also in its solutions makes possible considerable cost savings during transport and storage. A further advantage of TMT-Na$_2$.6 H$_2$O resides in its rather low alkalinity.

TMT-Na$_2$.6 H$_2$O can be used as a precipitation agent for separating heavy metals from aqueous phase, especially from waste water or process water. The precipitation of the slightly soluble heavy-metal salts of TMT-H$_3$ takes place in a known manner - similar to the procedure used for the previously known TMT-Na salts and their aqueous solutions. The treatment of the aqueous phase usually takes place in a pH range of 8-10. TMT-Na$_2$ results, since there must be a reneutralization after the separation of heavy metal, in a lesser accumulation of neutral salt than the TMT-Na$_3$ which was used almost exclusively in the past.

The invention also provides a method of preparing TMT-Na$_2$.6 H$_2$O in which the trisodium salt of trimercapto-s-triazine nonahydrate (TMT-Na$_3$9 H$_2$O) is reacted with trimercapto-s-triazine (TMT-H$_3$) in a molar ratio of 2-2.1:1 at 30°-60° C. in aqueous medium by adding TMT-Na$_3$.9 H$_2$O and TMT-H$_3$ into water, with intensive mixing, in such an amount that a solution which is approximately saturated with the disodium salt of trimercapto-s-triazine is produced, the mixture is subsequently cooled to 0°-10° C., and the crystallized TMT-Na$_2$.6 H$_2$O is separated from the mother liquor and dried under mild conditions.

TMT-Na$_3$9 H$_2$O is preferably added in a slight excess in relation to the stoichiometric molar ratio of 2:1. If the starting materials themselves were produced from cyanuric chloride and Na$_2$S, NaSH or a NaSH/Na$_2$S mixture in aqueous medium, it is more economical to add them in filter-moist form instead of dried initial TMT products.

Filter-moist TMT-Na$_2$.6 H$_2$O loses residual moisture by evaporation when stored in air until the TMT-Na$_2$ content is approximately 67 % by weight and the water of crystallization content is approximately 33% by weight. The drying can take place at 20°-30° C. under reduced pressure and/or via drying agents.

The structure of TMT-Na$_2$6 H$_2$O is determined by means of the following methods: 1. Identification by acidification and comparison with the pattern for TMT-H$_3$; 2. Determination of contents by acid-base titration; 3. Determination of purity by HPLC; 4. Water determination. When TMT-Na$_2$.6 H$_2$O is heated, water of crystallization is split off above 35° C. The splitting off takes place in several stages and is concluded at 149° C. (thermogravimetry (TG) and dynamic differential calorimetry (OSC)).

It is possible to produce crystalline TMT-Na$_2$6 H$_2$O directly from cyanuric chloride, NaSH and NaOH in a manner similar to that described for TMT-Na$_3$.9 H$_2$O in Published German Patent Application DE-OS 37 29 029; however, this is less advantageous. In distinction to TMT-Na$_3$.9 H$_2$O, TMT-Na$_2$.6 H$_2$O is more difficult to filter from the reaction mixture containing sodium chloride, for which reason high residual moisture, which additionally contains sodium chloride arising from the preparation, remains in the product. Moreover, after the crystallization of TMT-Na$_2$.6 H$_2$O the mother liquor still contains considerable amounts of this salt because of its high water solubility, which must be obtained by precipitation as TMT-H$_3$.

Both crystalline TMT-Na$_2$.6 H$_2$O in accordance with the invention as well as concentrated solutions of this salt can be obtained in a simple manner and practically free of sodium chloride by means of the changes indicated below in the method of preparation for TMT-Na$_3$.9 H$_2$O from cyanuric chloride described in Published German Patent Application DE-OS 37 29 029.

These changes consist of adjusting the conditions of crystallization for TMT-Na$_3$.9 H$_2$O, after the conclusion of the reaction of cyanuric chloride with NaSH or NaSH/Na$_2$S and NaOH, by raising the temperature and/or adding water and/or adjusting to a lower pH, in such a manner that only a part, preferably approximately two thirds, of the TMT-Na salts crystallize out as TMT-Na$_3$.9 H$_2$O. After separation of the salt and an optional washing with water, TMT-H$_3$ is precipitated from the combined filtrates - mother liquor and wash water - by adding a mineral acid, preferably hydrochloric acid, separated and optionally washed. The moist filter cake TMT-Na$_3$.9 H$_2$O and the moist filter cake TMT-H$_3$ are charged into a small amount of water in a molar ratio of approximately 2-2.1:1 at 40°-50° C. and reacted with one another. Preferably, such an amount of TMT-Na$_3$.9 H$_2$O and TMT-H$_3$ is charged into water that the saturation limit of TMT-Na$_2$ has been approximately attained and the mixture is then cooled down until the TMT-Na$_2$.6 H$_2$O is crystallized. If a solution which is not saturated with TMT-Na$_2$ is present at first, this solution can be concentrated by distilling off water under reduced pressure at moderate temperature, before the crystallization of the TMT-Na$_2$.6 H$_2$O.

The advantage of this embodiment of the invention is that only a maximum of 33% of the trimercapto-s-triazine formed from cyanuric chloride has to be isolated in an intermediate step as TMT-H$_3$, that the method can be carried out in a simple manner and that products are obtained which are practically free of sodium chloride.

DETAILED DESCRIPTION OF PREFERRED EMBODIMENTS

The invention is illustrated by the following examples.

EXAMPLE 1

172 g of 40% by weight aqueous NaSH (1.23 moles) are diluted with 112 ml water. 75 g cyanuric chloride (0.41 mole) and 60 g 50% by weight aqueous NaOH (0.75 mole) are added at 50° C. in such a manner that the pH is maintained between 9.5 and 10.5 and the temperature at 50° C. After the end of the addition, the mixture is agitated 1 hour longer at 50° C. and subsequently adjusted to a pH of 12.5 by means of the addition of 39 g 50% by weight aqueous NaOH (0.48 mole). After the mixture has cooled down to 10° C., it is centrifuged and the filter cake washed with 50 ml 20° C. water on the centrifuge.

The solid weighs 119.2 g and contains 54.1% by weight TMT-Na$_3$ in addition to water and traces of sodium chloride (less than 0.3% by weight). Filtrate and wash water are combined and acidified with 50 g concentrated hydrochloric acid and the TMT-H$_3$ which is precipitated quantitatively is filtered and washed free of sodium chloride with water. The washed TMT-H$_3$ filter cake weighs 59.0 g and contains 34.3% by weight TMT-H$_3$.

The filter cakes are stirred into 120 ml water. 298 g of a TMT solution are produced in which 0.38 mole TMT-Na salts are dissolved. This corresponds to a yield of 93.3% relative to cyanuric chloride used. 2.09 atoms of hydrogen of the TMT-H$_3$ are replaced by sodium. This is an approximately 28% by weight TMT-Na$_2$ solution.

EXAMPLE 2

296 g of the solution obtained according to Example 1 are condensed by evaporation in a vacuum at 50° C. until 115 ml water have been distilled off. As the mixture is cooled to 10° C., solid crystallizes out which is separated by filtration. 129 g solid are isolated which contains 51.5% by weight TMT-Na$_2$ and 48.5% by weight H$_2$O (free H$_2$O and H$_2$O bound as water of crystallization), as well as 51 g filtrate containing 34% by weight TMT-Na$_2$ TMT-Na$_2$.6 H$_2$O is obtained by carefully drying the solid in air.

EXAMPLE 3

90 g filter-moist TMT-Na$_3$.9 H$_2$O (54% by weight TMT-Na$_3$) (=0.2 mole) and 50 g filter-moist TMT-H$_3$ (34% by weight TMT-H$_3$) (=0.096 mole) are added in portions to 20 ml water with agitation while the temperature is maintained at 50° C. and the molar ratio at 2:1. A highly concentrated, practically clear solution of TMT-Na$_2$ is obtained which is subsequently cooled to approximately 5° C., during which time TMT-Na$_2$.6 H$_2$O crystallizes out. After separation of the crystallized product by filtration or centrifugation, the mother liquor can be reused for the reaction.

EXAMPLE 4

15 g Na$_2$S (0.19 mole) and 48 g NaHS (0.8 mole) are placed in 133 ml water in a vessel and 65 g cyanuric chloride (0.35 mole) are added at 40° C. in such a manner that the temperature is maintained. The pH drops at first to 9 and is maintained at that value by means of the simultaneous addition of a 30% by weight aqueous NaOH until all the cyanuric chloride has been added. After one half hour postreaction time, the pH is elevated to above 12.5 by adding the remainder of the total of 115 g sodium hydroxide solution (0.86 mole). The workup takes place in a customary manner; however, the mixture is crystallized at 30° C. and the TMT-Na$_3$ is not washed.

101 g filter cake is obtained containing 52.3% by weight TMT-Na$_3$, 1.5% by weight sodium chloride and 46.2% by weight water as well as 45 g filter cake containing 35.2% by weight TMT-H$_3$ and 64.8% by weight water. TMT-Na$_2$.6 H$_2$O is obtained by reacting the filter cakes in the molar ratio of 2:1 in accordance with Example 3.

What is claimed is:

1. The disodium salt of trimercapto-s-triazine hexahydrate (TMT-Na$_2$.6 H$_2$O).

2. A method of preparing the compound according to claim 1 which comprises reacting the trisodium salt of trimercapto-s-triazine nonahydrate (TMT-Na$_3$.9 H$_2$O) with trimercapto-s-triazine (TMT-H$_3$) in a molar ratio of 2–2.1:1 at 30°–60° C. in aqueous medium by adding TMT-Na$_3$.9 H$_2$O and TMT-H$_3$ into water with intensive mixing in such an amount that a solution which is approximately saturated with the disodium salt of trimercapto-s-triazine is produced, subsequently cooling the mixture to 0°–10° C., separating the crystallized TMT-Na$_2$.6 H$_2$O from the mother liquor and drying under protective conditions.

* * * * *